US008158153B2

(12) United States Patent
Liversidge et al.

(10) Patent No.: US 8,158,153 B2
(45) Date of Patent: Apr. 17, 2012

(54) NANOPARTICULATE BISPHOSPHONATE COMPOSITIONS

(75) Inventors: Gary G. Liversidge, West Chester, PA (US); Scott Jenkins, Downingtown, PA (US)

(73) Assignee: Alkermes Pharma Ireland Limited, Athlone, County Westmeath (IE)

( * ) Notice: Subject to any disclaimer, the term of this patent is extended or adjusted under 35 U.S.C. 154(b) by 435 days.

(21) Appl. No.: 11/377,650

(22) Filed: Mar. 17, 2006

(65) Prior Publication Data

US 2006/0210639 A1  Sep. 21, 2006

Related U.S. Application Data

(60) Provisional application No. 60/662,693, filed on Mar. 17, 2005.

(51) Int. Cl.
  A61K 9/14    (2006.01)
  A61K 31/66   (2006.01)
  A61K 9/127   (2006.01)

(52) U.S. Cl. ........ 424/489; 424/400; 424/450; 424/490; 514/75; 514/102; 514/824

(58) Field of Classification Search .................. 424/458, 424/459, 461, 463, 450, 464
See application file for complete search history.

(56) References Cited

U.S. PATENT DOCUMENTS

| | | |
|---|---|---|
| 3,422,021 A | 1/1969 | Roy |
| 4,621,077 A | 11/1986 | Rosini et al. |
| 4,761,406 A | 8/1988 | Flora et al. |
| 4,783,484 A | 11/1988 | Violante et al. |
| 4,826,689 A | 5/1989 | Violanto et al. |
| 4,876,248 A | 10/1989 | Breliere et al. |
| 4,922,007 A | 5/1990 | Kieczykowski et al. |
| 4,927,814 A | 5/1990 | Gall et al. |
| 4,970,335 A | 11/1990 | Isomura et al. |
| 4,997,454 A | 3/1991 | Violante et al. |
| 5,019,651 A | 5/1991 | Kieczykowski |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,358,941 A | 10/1994 | Bechard et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,591,730 A | 1/1997 | Stoller et al. |
| 5,593,657 A | 1/1997 | Ruddy et al. |
| 5,616,571 A | 4/1997 | Daifotis et al. |
| 5,622,721 A * | 4/1997 | Dansereau et al. ........... 424/490 |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |

(Continued)

FOREIGN PATENT DOCUMENTS

| | | |
|---|---|---|
| BE | 672.205 | 5/1966 |
| EP | 1 251 857 B1 | 2/2006 |
| WO | WO 2005/105068 A1 | 11/2005 |
| WO | WO 2005/107714 A2 | 11/2005 |
| WO | WO 2005/115331 A2 | 12/2005 |

OTHER PUBLICATIONS

Lindahl et al., "Characterization of Fluids from the Stomach and Proximal Jejunum in Men and Women", *Pharmaceutical Research*, vol. 14, No. 4, pp. 497-50 (1997).
The Merck Index, 10th Ed., p. 7581 (Merck & Co., Rahway, NJ, 1983).
Quimby et al., Tetrasodium Carbonyldiphosphonate, Synthesis, Reactions, and Spectral Properties (1967) pp. 4111-4114.
E.G. Lufkin et al., Pamidronate: An Urecognized Problem in Gastrointestinal Tolerability, Osteoporosis International, 4:320-322 (1994).
U.A. Liberman et al., Essophagitis and Alendronate, New England Journal of Medicine, vol. 335, No. 124, pp. 1069-1070 (1996).
P.C. De Groen, et al., Esophagitis Associated with the Use of Alendronate, New England Journal of Medicine, vol. 335, No. 124, pp. 1016-1021 (1996).

(Continued)

*Primary Examiner* — Michael G Hartley
*Assistant Examiner* — Jagadishwar Samala
(74) *Attorney, Agent, or Firm* — Foley & Lardner LLP

(57) ABSTRACT

Nanoparticulate bisphosphonate compositions, having an effective average particle size of less than 2000 nm, are described. The compositions are useful in treating bone resorption in a mammal.

12 Claims, No Drawings

U.S. PATENT DOCUMENTS

| | | | |
|---|---|---|---|
| 5,681,590 | A | 10/1997 | Bechard et al. |
| 5,718,388 | A | 2/1998 | Czekai et al. |
| 5,718,919 | A | 2/1998 | Ruddy et al. |
| 5,741,522 | A | 4/1998 | Violante et al. |
| 5,747,001 | A | 5/1998 | Wiedmann et al. |
| 5,776,496 | A | 7/1998 | Violante et al. |
| 5,834,025 | A | 11/1998 | De Garavilla et al. |
| 5,849,726 | A | 12/1998 | Brenner et al. |
| 5,862,999 | A | 1/1999 | Czekai et al. |
| 5,994,329 | A | 11/1999 | Daifotis et al. |
| 6,008,207 | A | 12/1999 | Brenner et al. |
| 6,015,801 | A | 1/2000 | Daifotis et al. |
| 6,045,829 | A | 4/2000 | Liversidge et al. |
| 6,068,858 | A | 5/2000 | Liversidge et al. |
| 6,090,410 | A | 7/2000 | Bechard et al. |
| 6,153,225 | A | 11/2000 | Lee et al. |
| 6,165,506 | A | 12/2000 | Jain et al. |
| 6,194,004 | B1 | 2/2001 | Bechard et al. |
| 6,221,400 | B1 | 4/2001 | Liversidge et al. |
| 6,225,294 | B1 | 5/2001 | Daifotis et al. |
| 6,264,922 | B1 | 7/2001 | Wood et al. |
| 6,267,989 | B1 | 7/2001 | Liversidge et al. |
| 6,270,806 | B1 | 8/2001 | Liversidge et al. |
| 6,316,029 | B1 | 11/2001 | Jain et al. |
| 6,333,316 | B1 | 12/2001 | Daifotis et al. |
| 6,375,986 | B1 | 4/2002 | Ryde et al. |
| 6,428,814 | B1 | 8/2002 | Bosch et al. |
| 6,431,478 | B1 | 8/2002 | Reed et al. |
| 6,432,381 | B2 | 8/2002 | Liversidge et al. |
| 6,432,932 | B1 | 8/2002 | Daifotis et al. |
| 6,465,443 | B2 | 10/2002 | Daifotis et al. |
| 6,468,559 | B1 * | 10/2002 | Chen et al. .................... 424/451 |
| 6,544,967 | B2 | 4/2003 | Daifotis et al. |
| 6,582,285 | B2 | 6/2003 | Czekai et al. |
| 6,592,903 | B2 | 7/2003 | Ryde et al. |
| 6,656,504 | B1 | 12/2003 | Bosch et al. |
| 6,676,965 | B1 | 1/2004 | Lulla et al. |
| 6,677,320 | B2 * | 1/2004 | Diederich et al. ............ 514/102 |
| 6,719,998 | B1 * | 4/2004 | Golomb et al. ............... 424/450 |
| 6,742,734 | B2 | 6/2004 | Reed et al. |
| 6,745,962 | B2 | 6/2004 | Reed et al. |
| 6,811,767 | B1 | 11/2004 | Bosch et al. |
| 6,908,626 | B2 | 6/2005 | Cooper et al. |
| 6,969,529 | B2 | 11/2005 | Bosch et al. |
| 6,976,647 | B2 | 12/2005 | Reed et al. |
| 6,991,191 | B2 | 1/2006 | Reed et al. |
| 2002/0012675 | A1 | 1/2002 | Jain et al. |
| 2002/0187184 | A1 * | 12/2002 | Golomb et al. ............... 424/450 |
| 2003/0236192 | A1 * | 12/2003 | Dasch et al. .................... 514/12 |
| 2004/0208925 | A1 | 10/2004 | Oner et al. |
| 2005/0260262 | A1 * | 11/2005 | Dansereau et al. ........... 424/464 |

OTHER PUBLICATIONS

D.O. Castell, Pill Esophagitis—The Case of Alendronate, New England Journal of Medicine, vol. 335, No. 124, pp. 1058-1059 (1996).

C.H. Chestnut et al., Alendronate Treatment of the Postmenopausal Osteoporotic Woman: Effect of Multiple Dosages on bone Mass and Bone Remodeling, the American Journal of Medicine, vol. 99, pp. 144-152 (Aug. 1995).

\* cited by examiner

NANOPARTICULATE BISPHOSPHONATE COMPOSITIONS

FIELD OF THE INVENTION

The invention relates to nanoparticulate bisphosphonate compositions, including multiparticulate or monolithic oral controlled release compositions and injectable formulations comprising nanoparticulate bisphosphonate. The compositions are useful for the treatment of disorders relating to abnormal bone resorption in a mammal, in particular, a human.

BACKGROUND OF THE INVENTION

A. Background Regarding Bisphosphonates

The methods and compositions of the invention comprise a bisphosphonate. The bisphosphonates of the invention are also referred to interchangeably as the "compounds of bisphosphonate." "Bisphosphonates are a class of drugs used to strengthen bone. Bone is in a constant state of remodeling, whereby new bone is laid down by cells called osteoblasts while old bone is removed by cells called osteoclasts. Bisphosphonates inhibit bone removal (resorption) by the osteoclasts. Bisphosphonates are used to treat osteoporosis and the bone pain from diseases such as metastatic breast cancer, multiple myeloma, and Paget's disease. The bisphosphonates include FOSAMAX® (alendronate sodium), AREDIA® (pamidronate sodium), ACTONEL® (risedronate sodium), BONIVA® (ibandronate sodium), DIDRONEL® (etidronate), and ZOMETA® (zolendronic acid). The compounds are also used to treat osteoporosis that is caused by treatment with a corticosteroid.

1. Background Regarding Alendronate

Alendronate sodium, which is commercially marketed as FOSAMAX®, is a bisphosphonate that acts as a specific inhibitor of osteoclast-mediated bone resorption. Bisphosphonates are synthetic analogs of pyrophosphate that bind to the hydroxyapatite found in bone. Alendronate sodium is chemically described as (4-amino-1-hydroxybutylidene) bisphosphonic acid monosodium salt trihydrate.

The empirical formula of alendronate sodium is $C_4H_{12}NNaO_7P_2 \cdot 3H_2O$ and its formula weight is 325.12. The structural formula is:

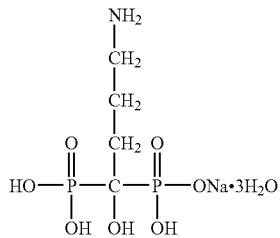

Alendronate sodium is a white, crystalline, nonhygroscopic powder. It is soluble in water, very slightly soluble in alcohol, and practically insoluble in chloroform.

FOSAMAX® tablets for oral administration (Merck & Co. of Rahway, N.J.) contain 6.53, 13.05, 45.68, 52.21 or 91.37 mg of alendronate monosodium salt trihydrate, which is the molar equivalent of 5, 10, 35, 40 and 70 mg, respectively, of free acid, and the following inactive ingredients: microcrystalline cellulose, anhydrous lactose, croscarmellose sodium, and magnesium stearate. FOSAMAX® 10 mg tablets also contain carnauba wax.

Disadvantages of FOSAMAX® include very poor bioavailability, fed/fasted variability in absorption, and significant gastrointestinal irritation.

As to the clinical pharmacological mechanism for alendronate sodium, animal studies have indicated the following mode of action. At the cellular level, alendronate shows preferential localization to sites of bone resorption, specifically under osteoclasts. The osteoclasts adhere normally to the bone surface but lack the ruffled border that is indicative of active resorption. Alendronate does not interfere with osteoclast recruitment or attachment, but it does inhibit osteoclast activity. Studies in mice on the localization of radioactive [$^3$H]alendronate in bone showed about 10-fold higher uptake on osteoclast surfaces than on osteoblast surfaces. Bones examined 6 and 49 days after [$^3$H]alendronate administration in rats and mice, respectively, showed that normal bone was formed on top of the alendronate, which was incorporated inside the matrix. While incorporated in bone matrix, alendronate is not pharmacologically active. Thus, alendronate must be continuously administered to suppress osteoclasts on newly formed resorption surfaces. Histomorphometry in baboons and rats showed that alendronate treatment reduces bone turnover (i.e., the number of sites at which bone is remodeled). In addition, bone formation exceeds bone resorption at these remodeling sites, leading to progressive gains in bone mass.

As to the pharmacokinetics of absorption of alendronate, relative to an intravenous (IV) reference dose, the mean oral bioavailability of alendronate in women was 0.64% for doses ranging from 5 to 70 mg when administered after an overnight fast and two hours before a standardized breakfast. Oral bioavailability of the 10 mg tablet in men (0.59%) was similar to that in women when administered after an overnight fast and 2 hours before breakfast.

A study examining the effect of timing of a meal on the bioavailability of alendronate was performed in 49 postmenopausal women. Bioavailability was decreased by approximately 40% when 10 mg alendronate was administered either 0.5 or 1 hour before a standardized breakfast, when compared to dosing 2 hours before eating. In studies of treatment and prevention of osteoporosis, alendronate was effective when administered at least 30 minutes before breakfast.

Bioavailability was negligible whether alendronate was administered with or up to two hours after a standardized breakfast. Concomitant administration of alendronate with coffee or orange juice reduced bioavailability by approximately 60%.

If oral administration of the bisphosphonate is desired, relatively high doses must be administered to compensate for the low bioavailability from the gastrointestinal tract. To offset this low bioavailability, it is generally recommended that the patient take the bisphosphonate on an empty stomach and fast for at least 30 minutes afterwards. However, many patients find the need for such fasting on a daily basis to be inconvenient. Moreover, oral administration has been associated with adverse gastrointestinal effects, especially those relating to the esophagus. See Fleisch, *Bisphosphonates In Bone Disease, From the Laboratory to the Patient*, 2$^{nd}$ Edition, Pantheon Publishing (1995). These effects appear to be related to the irritant potential of the bisphosphonate in the esophagus, a problem which is exacerbated by the presence of refluxed gastric acid. For example, the bisphosphonate, pamidronate has been associated with esophageal ulcers. See E. G. Lufkin et al., *Pamidronate: An Unrecognized Problem in Gastrointestinal Tolerability, Osteoporosis International*, 4: 320-322 (1994), which is incorporated by reference herein in its entirety. Although not as common, the use of alendronate has been associated with esophagitis and/or esophageal ulcers. See P. C. DeGroen, et al., *Esophagitis Associated With The Use Of Alendronate*, New England Journal of Medicine, vol. 335, no. 124, pp. 1016-1021 (1996), D. O. Castell, *Pill Esophagitis—The Case of Alendronate*, New England Journal of Medicine, vol. 335, no. 124, pp. 1058-1059 (1996), and U. A. Liberman et al., *Esophagitis and Alendronate*, New England Journal of Medicine, vol. 335, no. 124, pp. 1069-1070 (1996), which are incorporated by reference herein in their entirety. The degree of adverse gastrointestinal effects of bisphosphonates has been shown to increase with increasing dose. See C. H. Chestnut et al., *Alendronate Treatment of the Postmenopausal Osteoporotic Woman: Effect of Multiple Dosages on Bone Mass and Bone Remodeling*, The American Journal of Medicine, vol. 99, pp. 144-152, (August 1995, which is incorporated by reference herein in its entirety. Also, these adverse esophogeal effects appear to be more prevalent in patients who do not take the bisphosphonate with an adequate amount of liquid or who lie down shortly after dosing, thereby increasing the chance for esophageal reflux.

The interference with the bioavailability of alendronate sodium resulting from eating and drinking, and the adverse gastrointestinal effects of bisphosphonates are reflected in patient information for taking once weekly FOSAMAX® tablets. The guidelines prescribe that after swallowing a FOSAMAX® tablet one must wait at least 30 minutes before taking food, beverage or other medicaments of the day. The guidelines further require that FOSAMAX® tablets are not taken at bedtime or before getting up for the day. In addition, the patient must stay fully upright after taking FOSAMAX® for at least 30 minutes and after the first food of the day.

U.S. Pat. Nos. 5,616,571, 5,994,329, 6,015,801, 6,225,294, 6,333,316, 6,432,932, 6,465,443 and 6,544,967, all to Daifotis et al., U.S. Pat. No. 4,621,077 to Rosoni et al., U.S. Pat. Nos. 5,358,941, 5,681,590, 6,090,410 and 6,194,004, all to Bechard et al. and U.S. Pat. Nos. 5,849,726 and 6,008,207, both to Brenner et al., relate to the use of bisphosphonates in the treatment of abnormal bone resorption. These United States Patents are incorporated by reference.

2. Background Regarding Pamidronate

Pamidronate disodium, commercially available as AREDIA®, is a bone-resorption inhibitor available in 30-mg, 60-mg, or 90-mg vials for intravenous administration. Each 30-mg, 60-mg, and 90-mg vial contains, respectively, 30 mg, 60 mg, and 90 mg of sterile, lyophilized pamidronate disodium and 470 mg, 400 mg, and 375 mg of mannitol, USP. The pH of a 1% solution of pamidronate disodium in distilled water is approximately 8.3. AREDIA®, a member of the group of chemical compounds known as bisphosphonates, is an analog of pyrophosphate. Pamidronate disodium is designated chemically as phosphonic acid (3-amino-1-hydroxypropylidene) bis-, disodium salt, pentahydrate, (APD), and its structural formula is:

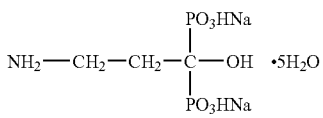

Pamidronate disodium is a white-to-practically-white powder. It is soluble in water and in 2N sodium hydroxide, sparingly soluble in 0.1N hydrochloric acid and in 0.1N acetic acid, and practically insoluble in organic solvents. Its molecular formula is $C_3H_9NO_7P_2Na_2.5H_2O$ and its molecular weight is 369.1. Inactive ingredients for AREDIA® include mannitol, USP, and phosphoric acid (for adjustment to pH 6.5 prior to lyophilization).

Side effects of pamidronate include pain at the site of catheter insertion (including redness, swelling or induration, and pain on palpation). Side effects also include gastrointestinal pain, including abdominal pain, anorexia, constipation, nausea, vomiting, diarrhea, dyspepsia, gastrointestinal hemorrhage, and stomatitis.

3. Background Regarding Risedronate

ACTONEL® (risedronate sodium tablets) is a pyridinyl bisphosphonate that inhibits osteoclast-mediated bone resorption and modulates bone metabolism. Each ACTONEL® tablet for oral administration contains the equivalent of 5, 30, or 35 mg of anhydrous risedronate sodium in the form of the hemi-pentahydrate with small amounts of monohydrate. The empirical formula for risedronate sodium hemi-pentahydrate is $C_7H_{10}NO_7P_2Na$ .2.5 $H_2O$. The chemical name of risedronate sodium is [1-hydroxy-2-(3-pyridinyl) ethylidene]bis[phosphonic acid] monosodium salt. The chemical structure of risedronate sodium hemi-pentahydrate is the following:

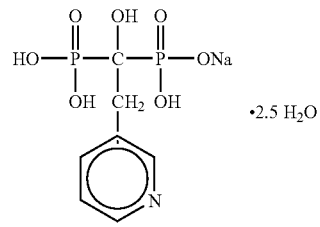

Risedronate sodium is a fine, white to off-white, odorless, crystalline powder. It is soluble in water and in aqueous solutions, and essentially insoluble in common organic solvents. Inactive ingredients in ACTONEL® include crospovidone, ferric oxide red (35-mg tablets only), ferric oxide yellow (5 and 35-mg tablets only), hydroxypropyl cellulose, hydroxypropyl methylcellulose, lactose monohydrate, magnesium stearate, microcrystalline cellulose, polyethylene glycol, silicon dioxide, and titanium dioxide.

Side effects of risedronate include gastrointestinal irritation.

4. Background Regarding Ibandronate

Ibandronate sodium is commercially sold as BONIVA®. BONIVA® is a nitrogen-containing bisphosphonate that inhibits osteoclast-mediated bone resorption. The chemical name for ibandronate sodium is 3-(N-methyl-N-pentyl) amino-1-hydroxypropane-1,1-diphosphonic acid, monosodium salt, monohydrate, with the molecular formula $C_9H_{22}NO_7P_2Na$. $H_2O$ and a molecular weight of 359.24. Ibandronate sodium is a white- to off-white powder. It is freely soluble in water and practically insoluble in organic solvents. Ibandronate sodium has the following structural formula:

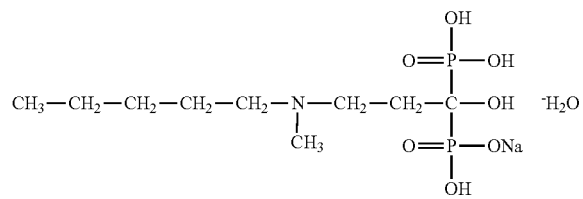

BONIVA® is available as a white, oblong, 2.5-mg film-coated tablet for daily oral administration or as a white, oblong, 150-mg film-coated tablet for once-monthly oral administration. One 2.5-mg film-coated tablet contains 2.813 mg ibandronate monosodium monohydrate, equivalent to 2.5 mg free acid. One 150-mg film-coated tablet contains 168.75 mg ibandronate monosodium monohydrate, equivalent to 150 mg free acid. BONIVA® also contains the following inactive ingredients: lactose monohydrate, povidone, microcrystalline cellulose, crospovidone, purified stearic acid, colloidal silicon dioxide, and purified water. The tablet film coating contains hypromellose, titanium dioxide, talc, polyethylene glycol 6000, and purified water.

Side effects of ibandronate include gastrointestinal irritation.

5. Background Regarding Etidronate

Etidronate is commercially available as DIDRONEL® (etidronate disodium). DIDRONEL® tablets contain either 200 mg or 400 mg of etidronate disodium, the disodium salt of (1-hydroxyethylidene) diphosphonic acid, for oral administration. This compound, also known as EHDP, regulates bone metabolism. It is a white powder, highly soluble in water, with a molecular weight of 250 and the following structural formula:

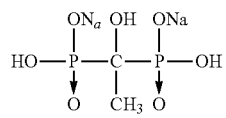

Inactive ingredients in DIDRONEL® tablets include magnesium stearate, microcrystalline cellulose, and starch.

Side effects of DIDRONEL® include gastrointestinal irritation, which can affect the dosage that can be administered. Also, because of potential gastrointestinal irritation, patients are advised to avoid consuming food within two hours of dosing.

6. Background Regarding Zolendronate

Zolendronate is commercially available as ZOMETA® (zolendronic acid). ZOMETA® contains zoledronic acid, a bisphosphonic acid which is an inhibitor of osteoclastic bone resorption. Zoledronic acid is designated chemically as (1-Hydroxy-2-imidazol-1-yl-phosphonoethyl) phosphonic acid monohydrate and its structural formula is

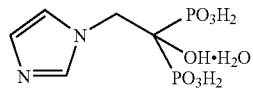

Zoledronic acid is a white crystalline powder. Its molecular formula is $C_5H_{10}N_2O_7P_2 \cdot H_2O$ and its molar mass is 290.1 g/Mol. Zoledronic acid is highly soluble in 0.1N sodium hydroxide solution, sparingly soluble in water and 0.1N hydrochloric acid, and practically insoluble in organic solvents. The pH of a 0.7% solution of zoledronic acid in water is approximately 2.0.

ZOMETA® (zoledronic acid) Injection is available in vials as a sterile liquid concentrate solution for intravenous infusion. Each 5-mL vial contains 4.264 mg of zoledronic acid monohydrate, corresponding to 4 mg zoledronic acid on an anhydrous basis. Inactive ingredients in ZOMETA® include mannitol, USP, as bulking agent, water for injection and sodium citrate, USP, as buffering agent.

Intravenous administration of ZOMETA® has been most commonly associated with fever. Gastrointestinal reactions such as nausea and vomiting have been reported following administration of ZOMETA®. Local reactions at the infusion site, such as redness or swelling, were also observed.

B. Background Regarding Nanoparticulate Active Agent Compositions

Nanoparticulate active agent compositions, first described in U.S. Pat. No. 5,145,684 ("the '684 patent"), comprise particles of a poorly soluble therapeutic or diagnostic agent having adsorbed onto or associated with the surface thereof a non-crosslinked surface stabilizer. The '684 patent also describes methods of making such nanoparticulate active agent compositions but does not describe compositions comprising bisphosphonates in nanoparticulate form. Methods of making nanoparticulate active agent compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470, 583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(-)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract;" U.S. Pat. No. 6,582,285 for "Apparatus for Sanitary Wet Milling;" and U.S. Pat. No. 6,592,903 for "Nanoparticulate Dispersions Comprising a Synergistic Combination of a Polymeric Surface Stabilizer and Dioctyl Sodium Sulfosuccinate;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" U.S. Pat. No. 6,976,647 for "System and Method for Milling Materials;" and U.S. Pat. No. 6,991,191 for "Method of Using a Small Scale Mill;" all of which are specifically incorporated by reference. In addition, U.S. Patent Application No. 20020012675 Al, published on Jan. 31, 2002, for "Controlled Release Nanoparticulate Compositions," describes nanoparticulate compositions and is specifically incorporated by reference. None of these references describe compositions of nanoparticulate bisphosphonates, nanoparticulate alendronate, nanoparticulate pamidronate, or nanoparticulate risedronate.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter" all of which are specifically incorporated herein by reference.

There is a need for compositions of bisphosphonates, such as alendronate, pamidronate, and risedronate, that have enhanced bioavailability and reduced adverse side effects, including reduced gastrointestinal irritation. The present invention satisfies these needs.

SUMMARY OF THE INVENTION

It is an object of the invention to provide nanoparticulate bisphosphonate compositions. Exemplary bisphosphonates include but are not limited to alendronate, pamidronate, risedronate, etidronate, ibandronate, and zolendronic acid. The nanoparticulate bisphosphonate has an effective average particle size of less than about 2000 nm. The compositions of the invention comprise at least one bisphosphonate and at least one surface stabilizer for the nanoparticulate bisphosphonate.

The compositions of the invention can be formulated into any pharmaceutically acceptable dosage form. The compositions can also one or more additional compounds useful in the treatment of disorders relating to abnormal bone resorption.

In one embodiment, the nanoparticulate bisphosphonate, such as alendronate, pamidronate, risedronate, etidronate, ibandronate, and zolendronic acid, is formulated into an injectable dosage form suitable for administration by intramuscular or subcutaneous means. In one embodiment, the injectable dosage form comprises a complex of nanoparticulate bisphosphonate and multivalent cations, such as $Ca^{++}$, in combination with at least one surface stabilizer.

In yet another embodiment of the invention, provided is an injectable dosage form of a stable nanoparticulate bisphosphonate, such as alendronate, pamidronate, risedronate, etidronate, ibandronate, or zolendronic acid, wherein the bisphosphonate is released from an injectable depot over a period of time. Such a dosage form is beneficial to patients suffering from disorders relating to abnormal bone resorption, as the dosage form provides therapeutic effects for extended periods of time, thereby improving efficacy and patient compliance. In one embodiment of the invention, the injectable depot dosage form provides therapeutic levels of drug for a period of up to about five years. The injectable dosage forms can comprise, for example, additional ingredients including biodegradable polymers, lipid complexes, and/or oil solutions which sequester the bisphosphonate and then slowly release the drug from the injection site.

It is another object of the invention to provide oral dosage forms of nanoparticulate bisphosphonate formulations which overcome the bioavailability problems and other problems associated with prior conventional bisphosphonate formulations, such as FOSAMAX®, AREDIA®, and ACTONEL®, including gastrointestinal irritation problems. The oral dosage form can additionally comprise a penetration enhancer, such as sodium caprylate, a chelating agent, a pH sensitive coating, or a combination thereof.

Another object of the invention is to provide solid oral dosage forms comprising a multiparticulate or monolithic composition comprising at least one nanoparticulate bisphosphonate, such as alendronate, pamidronate, risedronate, etidronate, ibandronate, or zolendronic acid, and at least one surface stabilizer, wherein the compositions have improved bioavailability and reduced adverse gastrointestinal effects as compared to conventional bisphosphonates.

Another object of the invention is a multiparticulate or monolithic oral composition of a nanoparticulate bisphosphonate, such as alendronate, pamidronate, risedronate, etidronate, ibandronate, and zolendronic acid, and at least one surface stabilizer, wherein a patient can take the composition just before bedtime or prior to getting up in the morning. Another object of the invention is a multiparticulate or monolithic oral composition of a nanoparticulate bisphosphonate, such as alendronate, pamidronate, risedronate, etidronate, ibandronate, and zolendronic acid, and at least one surface stabilizer, wherein the composition can be taken by a patient without requiring that the patient sit upright to avoid incurring the adverse gastrointestinal effects of bisphosphonates. Conventional bisphosphonate compositions, such as FOSAMAX®, AREDIA®, ACTONEL®, DIDRONEL®, BONIVA®, and ZOMETA®, cannot be taken just before bedtime or prior to getting up in the morning. Such conventional bisphosphonate compositions also require that the patient sit upright for at least 30 minutes following dosing to avoid incurring the adverse gastrointestinal effects of bisphosphonates. These limitations affect patient compliance with dosing instructions, and consequently effectiveness of the drugs.

The above objects are realized by a multiparticulate or monolithic composition comprising at least one nanoparticulate bisphosphonate, such as alendronate, pamidronate, risedronate, etidronate, ibandronate, and zolendronic acid, at least one surface stabilizer, and sodium caprylate. The composition may further comprise a chelating agent. The bisphosphonate particles are preferably coated with a pH-sensitive coating. Following oral delivery, the composition releases the bisphosphonate nanoparticles in the intestine, thereby avoiding gastrointestinal irritancy.

In another aspect of the invention there is provided a method of preparing a nanoparticulate bisphosphonate composition. The method comprises: (1) dispersing at least one bisphosphonate, such as alendronate, pamidronate, risedronate, etidronate, ibandronate, and zolendronic acid, in a liquid dispersion media in which the bisphosphonate is poorly soluble; and (2) mechanically reducing the particle size of the bisphosphonate to a desired effective average particle size, e.g., less than about 2000 nm. One or more surface stabilizers can be added to the composition before, during, or after particle size reduction of the bisphosphonate. In one embodiment, the bisphosphonate is complexed with multivalent cations, such as $Ca^{++}$, to reduce the water solubility of the bisphosphonate. Such complexing enables particle size reduction of the bisphosphonate in an aqueous media.

Following particle size reduction, the nanoparticulate bisphosphonate composition can be formulated into any pharmaceutically acceptable dosage form, such as an injectable or oral dosage form. In one embodiment, this invention further discloses a method of making multiparticulate or monolithic oral compositions of the nanoparticulate bisphosphonate compositions of the invention comprising the steps of mixing the nanoparticulate bisphosphonate, at least one surface stabilizer, sodium caprylate, and preferably, a chelating agent, such as EDTA or EGTA, followed by coating the drug particles with a pH-sensitive coating.

The invention is also directed to methods of treatment including but not limited to, the treatment of disorders relating to abnormal bone resorption, using the nanoparticulate bisphosphonate compositions of the invention. Such methods comprise administering to a subject a therapeutically effective amount of a nanoparticulate bisphosphonate composition of the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to nanoparticulate bisphosphonate compositions comprising at least one bisphosphonate, such as alendronate, pamidronate, risedronate, etidronate, ibandronate, and zolendronic acid, and at least one surface stabilizer, wherein the bisphosphonate particles have an effective average particle size of less than about 2000 nm.

Conventional tablets of bisphosphonates, such as FOSAMAX®, ACTONEL®, DIDRONEL®, and BONIVA®, have limited bioavailability. While bisphosphonates, such as alendronate, pamidronate, risedronate, etidronate, ibandronate, and zolendronate, are water soluble, which is generally associated with high bioavailability, upon administration conventional bisphosphonates often complex with cations in the surrounding environment and precipitate, thereby inhibiting cellular diffusion of the bisphosphonate, which is required for drug absorption. Moreover, conventional bisphosphonates do not diffuse well across the gut wall due to the high degree of polarity of the compounds.

The present invention encompasses nanoparticulate bisphosphonate compositions additionally comprising a chelating agent. The chelating agent is proposed to enhance the bioavailability of the bisphosphonate by bonding to the cations in the gastrointestinal tract; i.e., the chelating agent competes with the bisphosphonate for binding to the cations in the gastrointestinal tract, thereby reducing the quantity of bisphosphonate that binds to the cations in the GI tract. The presence of such a chelating agent would normally be expected further decrease the bioavailability of the bisphosphonate dosage form. However, reducing the particle size of the bisphosphonate to a nanoparticulate size, which dramatically increases the surface area of the drug, results in a bisphosphonate composition with significantly improved bioavailability as compared to conventional bisphosphonate dosage forms.

In another embodiment of the invention, the nanoparticulate bisphosphonate can be complexed with a multivalent cation, such as $Ca^{++}$ or other salt that is poorly water soluble, or esters or prodrugs that are poorly water soluble. Such complexing enables particle size reduction of the bisphosphonate in an aqueous media.

Bisphosphonate bioavailability can be further improved by mixing particles of the bisphosphonate with sodium caprylate particles, thereby allowing a smaller dose to give the same in vivo blood levels as larger dosage amounts required in the past. Moreover, for oral dosage forms, the bisphosphonate particles can be coated with a pH-sensitive coating that delays diffusion of the contents of the particles until the particles reach the intestine. Accordingly, the coated particles lessen possible unwanted side effects resulting from the release of currently used conventional bisphosphonates in the gastrointestinal tract.

The methods and compositions of the invention are useful for inhibiting bone resorption and for treating and preventing abnormal bone resorption and conditions associated therewith. Such conditions include both generalized and localized bone loss. Also, the creation of bone having an abnormal structure, as in Paget's disease, can be associated with abnormal bone resorption. The term "generalized bone loss" means bone loss at multiple skeletal sites or throughout the skeletal system. The term "localized bone loss" means bone loss at one or more specific, defined skeletal sites.

Generalized bone loss is often associated with osteoporosis. Osteoporosis is most common in post-menopausal women, whose estrogen production has been greatly diminished. However, osteoporosis can also be steroid-induced and has been observed in males due to age. Osteoporosis can be induced by disease, e.g., rheumatoid arthritis, it can be induced by secondary causes, e.g., glucocorticoid therapy, or it can about with no identifiable cause, i.e., osteoporosis. In the present invention, preferred methods include the treatment or prevention of abnormal bone resorption in osteoporotic humans.

Localized bone loss has been associated with periodontal disease, bone fractures, and with periprosthetic osteolysis (in other words where bone resorption has occurred in proximity to a prosthetic implant).

Generalized or localized bone loss can occur from disuse, which is often a problem for those confined to a bed or a wheelchair, or for those who have an immobilized limb set in a cast or in traction.

The methods and compositions of the invention are useful for treating and/or preventing the following conditions or disease states: osteoporosis, which can include post-menopausal osteoporosis, steroid-induced osteoporosis, male osteoporosis, disease-induced osteoporosis, idiopathic osteoporosis; Paget's disease; abnormally increased bone turnover; periodontal disease; localized bone loss associated with periprosthetic osteolysis; and bone fractures.

Advantages of the nanoparticulate bisphosphonate compositions of the invention as compared to conventional bisphosphonate dosage forms, such as FOSAMAX®, AREDIA®, ACTONEL®, DIDRONEL®, BONIVA®, and ZOMETA®; include but are not limited to: (1) increased bioavailability; (2) reduced gastrointestinal irritation; (3) decreased pain upon administration for injectable bisphosphonate dosage forms of the invention; (4) smaller tablet or other solid dosage form size; (5) smaller doses of bisphosphonate required to obtain the same pharmacological effect; (6) improved pharmacokinetic profiles; (7) bioequivalency of the bisphosphonate compositions of the invention when administered under fed as compared to fasting conditions; (8) an increased rate of dissolution; (9) bioadhesive bisphosphonate compositions of the invention; and (10) the compositions of the invention can be used in conjunction with other active agents useful for the treatment of disorders relating to abnormal bone resorption.

The invention also includes nanoparticulate bisphosphonate compositions comprising one or more non-toxic physiologically acceptable carriers, adjuvants, or vehicles, collectively referred to as carriers. The compositions can be formulated for parenteral injection (e.g., intramuscular, or subcutaneous as a depot), oral administration in solid, liquid, or aerosol form, vaginal, nasal, otic, rectal, ocular, local (powders, ointments or drops), buccal, intracisternal, intraperitoneal, or topical administration, and the like.

Although exemplary dosage forms of the invention are a solid dosage form and an injectable dosage form, any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, or a combination thereof. A solid dose tablet formulation is preferred. In a preferred form, a quantity of the injectable formulation is maintained in a depot for continuous release to the human patient by intramuscular or subcutaneous injection.

A. Definitions

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to particles of the bisphosphonate, "stable" means that the bisphosphonate particles do not appreciably flocculate or agglomerate due to interparticle attractive forces or otherwise spontaneously increase in particle size.

The term "effective average particle size of less than about 2000 nm" as used herein means that at least 50% of the bisphosphonate particles have a size, by weight, of less than about 2000 nm, when measured by, for example, sedimentation field flow fractionation, photon correlation spectroscopy, light scattering, disk centrifugation, and other techniques known to those of skill in the art.

The term "conventional" or "non-nanoparticulate" bisphosphonate means a bisphosphonate which is solubilized or which has an effective average particle size of greater than about 2000 nm. Nanoparticulate active agents as defined herein have an effective average particle size of less than about 2000 nm.

As used herein, the phrase "therapeutically effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The term "abnormal bone resorption," as used herein means a degree of bone resorption that exceeds the degree of bone formation, either locally, or in the skeleton as a whole. Alternatively, "abnormal bone resorption" can be associated with the formation of bone having an abnormal structure.

The term "inhibiting bone resorption," as used herein, means treating or preventing bone resorption by the direct or indirect alteration of osteoclast formation or activity. Inhibition of bone resorption refers to treatment or prevention of bone loss, especially the inhibition of removal of existing bone either from the mineral phase and/or the organic matrix phase, through direct or indirect alteration of osteoclast formation or activity.

The term "particulate" as used herein refers to a state of matter which is characterized by the presence of discrete particles, pellets, beads or granules irrespective of their size, shape or morphology. The term "multiparticulate" as used herein means a plurality of discrete, or aggregated, particles, pellets, beads, granules or mixture thereof irrespective of their size, shape or morphology.

B. Preferred Characteristics of the Bisphosphonate Compositions of the Invention 1. Increased Bioavailability The nanoparticulate bisphosphonate, such as alendronate, pamidronate, risedronate, etidronate, ibandronate, and zolendronic acid, compositions of the invention, including the oral dosage forms, are proposed to exhibit increased bioavailability and require smaller doses as compared to prior conventional bisphosphonate compositions, such as FOSAMAX®, AREDIA®, ACTONEL®, DIDRONEL®, BONIVA®, and ZOMETA®.

For nanoparticulate bisphosphonate compositions comprising a chelating agent, the particles of chelating agent improve the bioavailability of the bisphosphonate by binding to cations in the gastrointestinal tract. For certain dosage forms, such as oral dosage forms, the bioavailability of the nanoparticulate bisphosphonate is also improved by the addition of sodium caprylate. Also for certain dosage forms, such as oral dosage forms, coating of the bisphosphonate particles with a pH sensitive coating to prevent dissolution before the bisphosphonate reaches the small intestine decreases the adverse effects to the esophagus and the stomach.

Smaller bisphosphonate dosages, such as those enabled by nanoparticulate bisphosphonate compositions, benefit a patient by reducing the potential for producing the adverse gastrointestinal effects that can result from the administration of conventional, non-nanoparticulate bisphosphonates, and in particular, alendronate sodium. These effects may occur in the esophagus, stomach, intestines and rectum, particularly the upper gastrointestinal tract, i.e., the esophagus and stomach. Non-limiting adverse gastrointestinal effects for conventional bisphosphonates, such as FOSAMAX®, AREDIA®, ACTONEL®, DIDRONEL®, BONIVA®, and ZOMETA®, include but are not limited to GERP, esophagitis, dyspepsia, ulcers, esophageal irritation, esophageal perforation, abdominal pain, and constipation.

2. The Pharmacokinetic Profiles of the Nanoparticulate Bisphosphonate Compositions of the Invention are not Affected by the Fed or Fasted State of the Subject Ingesting the Compositions The compositions of the invention encompass a nanoparticulate bisphosphonate, such as alendronate, pamidronate, risedronate, etidronate, ibandronate, and zolendronic acid, wherein the pharmacokinetic profile of the bisphosphonate is not substantially affected by the fed or fasted state of a subject ingesting the composition. This means that there is little or no appreciable difference in the quantity of bisphosphonate absorbed or the rate of drug absorption when the nanoparticulate compositions comprising a nanoparticulate bisphosphonate, such as alendronate, pamidronate, risedronate, etidronate, ibandronate, and zolendronic acid, are administered in the fed versus the fasted state.

Benefits of a dosage form which substantially eliminates the effect of food include an increase in subject convenience, thereby increasing subject compliance, as the subject does not need to ensure that they are taking a dose either with or without food. This is significant, as with poor subject compliance with a bisphosphonate, alendronate, pamidronate, risedronate, etidronate, ibandronate, and zolendronic acid, an increase in the medical condition for which the drug is being prescribed may be observed.

The invention also preferably provides compositions comprising at least one nanoparticulate bisphosphonate, such as alendronate, pamidronate, risedronate, etidronate, ibandronate, and zolendronic acid, having a desirable pharmacokinetic profile when administered to mammalian subjects. The desirable pharmacokinetic profile of the compositions comprising at least one bisphosphonate preferably includes, but is not limited to: (1) a $C_{max}$ for the bisphosphonate, such as alendronate, pamidronate, risedronate, etidronate, ibandronate, and zolendronic acid, when assayed in the plasma of a mammalian subject following administration, that is preferably greater than the $C_{max}$ for a non-nanoparticulate formulation of the same bisphosphonate (e.g., FOSAMAX®, AREDIA®, ACTONEL®, DIDRONEL®, BONIVA®, and ZOMETA®), administered at the same dosage; and/or (2) an AUC for the bisphosphonate, such as alendronate, pamidronate, risedronate, etidronate, ibandronate, and zolendronic acid, when assayed in the plasma of a mammalian subject following administration, that is preferably greater than the AUC for a non-nanoparticulate formulation of the same bisphosphonate (e.g., FOSAMAX®, AREDIA®, ACTONEL®, DIDRONEL®, BONIVA®, and ZOMETA®), administered at the same dosage; and/or (3) a $T_{max}$ for the bisphosphonate, such as alendronate, pamidronate, risedronate, etidronate, ibandronate, and zolendronic acid, when assayed in the plasma of a mammalian subject following administration, that is preferably less than the $T_{max}$ for a non-nanoparticulate formulation of the same bisphosphonate (e.g., FOSAMAX®, AREDIA®, ACTONEL®, DIDRONEL®, BONIVA®, and ZOMETA®), administered at the same dosage. The desirable pharmacokinetic profile, as used herein, is the pharmacokinetic profile measured after the initial dose of the bisphosphonate.

In one embodiment, a composition comprising at least one nanoparticulate bisphosphonate, such as alendronate, pamidronate, risedronate, etidronate, ibandronate, and zolendronic acid, exhibits in comparative pharmacokinetic testing with a non-nanoparticulate formulation of the same bisphosphonate (e.g., FOSAMAX®, AREDIA®, ACTONEL®, DIDRONEL®, BONIVA®, and ZOMETA®), administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the non-nanoparticulate bisphosphonate formulation.

In another embodiment, the composition comprising at least one nanoparticulate bisphosphonate, such as alendronate, pamidronate, risedronate, etidronate, ibandronate, and zolendronic acid, exhibits in comparative pharmacokinetic testing with a non-nanoparticulate formulation of the same bisphosphonate (e.g., FOSAMAX®, AREDIA®, ACTONEL®, DIDRONEL®, BONIVA®, and ZOMETA®), administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate bisphosphonate formulation.

In yet another embodiment, the composition comprising at least one nanoparticulate bisphosphonate, such as alendronate, pamidronate, risedronate, etidronate, ibandronate, and zolendronic acid, of the invention exhibits in comparative pharmacokinetic testing with a non-nanoparticulate formulation of the same bisphosphonate (e.g., FOSAMAX®, AREDIA®, ACTONEL®, DIDRONEL®, BONIVA®, and ZOMETA®), administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate bisphosphonate formulation.

3. Bioequivalency of the Bisphosphonate Compositions of the Invention When Administered in the Fed Versus the Fasted State The invention also encompasses a composition comprising at least one nanoparticulate bisphosphonate, such as alendronate, pamidronate, risedronate, etidronate, ibandronate, and zolendronic acid, in which administration of the composition to a subject in a fasted state is bioequivalent to administration of the composition to a subject in a fed state. The difference in absorption of the compositions comprising the nanoparticulate bisphosphonate when administered in the fed versus the fasted state, is preferably less than about 35%, less than about 30%, less than about 25%, less than about 20%, less than about 15%, less than about 10%, less than about 5%, or less than about 3%.

In one embodiment of the invention, the invention encompasses compositions comprising at least one nanoparticulate bisphosphonate, such as alendronate, pamidronate, risedronate, etidronate, ibandronate, and zolendronic acid, wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA).

Under U.S. FDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

4. Dissolution Profiles of the Bisphosphonate Compositions of the Invention

The compositions of the invention comprising at least one nanoparticulate bisphosphonate, such as alendronate, pamidronate, risedronate, etidronate, ibandronate, and zolendronic acid, have unexpectedly dramatic dissolution profiles. Rapid dissolution of an administered bisphosphonate is preferable, as faster dissolution generally leads to faster onset of action and greater bioavailability. To improve the dissolution profile and bioavailability of comprising at least one nanoparticulate bisphosphonate, it is useful to increase the drug's dissolution so that it could attain a level close to 100%.

The compositions of the invention comprising at least one nanoparticulate bisphosphonate preferably have a dissolution profile in which within about 5 minutes at least about 20% of the composition is dissolved. In other embodiments of the invention, at least about 30% or at least about 40% of the composition comprising at least one nanoparticulate bisphosphonate is dissolved within about 5 minutes. In yet other embodiments of the invention, preferably at least about 40%, at least about 50%, at least about 60%, at least about 70%, or at least about 80% of the composition comprising at least one nanoparticulate bisphosphonate is dissolved within about 10 minutes. Finally, in another embodiment of the invention, preferably at least about 70%, at least about 80%, at least about 90%, or at least about 100% of the composition comprising at least one nanoparticulate bisphosphonate is dissolved within about 20 minutes.

Dissolution is preferably measured in a medium which is discriminating. Such a dissolution medium will produce two very different dissolution curves for two products having very different dissolution profiles in gastric juices, i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

5. Redispersibility Profiles of the Nanoparticulate Bisphosphonate Compositions of the Invention In one embodiment of the invention, the nanoparticulate bisphosphonate compositions of the invention are formulated into solid dose forms, including powders, which redisperse such that the effective average particle size of the redispersed bisphosphonate particles is less than about 2 microns. This is significant, as if upon administration the nanoparticulate bisphosphonate compositions did not redisperse to a nanoparticulate particle size, then the dosage form may lose the benefits afforded by formulating the bisphosphonate into a nanoparticulate particle size.

Indeed, the nanoparticulate bisphosphonate compositions of the invention benefit from the small particle size of the bisphosphonate; if the bisphosphonate does not redisperse into a small particle size upon administration, then "clumps" or agglomerated bisphosphonate particles are formed, owing to the extremely high surface free energy of the nanoparticulate system and the thermodynamic driving force to achieve an overall reduction in free energy. With the formation of such agglomerated particles, the bioavailability of the bisphosphonate dosage form may fall.

Moreover, the nanoparticulate bisphosphonate compositions of the invention exhibit dramatic redispersion of the nanoparticulate bisphosphonate particles upon administration to a mammal, such as a human or animal, as demonstrated by reconstitution/redispersion in a biorelevant aqueous media such that the effective average particle size of the redispersed bisphosphonate particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength. Such redispersion in a biorelevant media is predictive of in vivo efficacy of the bisphosphonate dosage form.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 N, and NaCl solutions, ranging in concentration from about 0.001 to about 0.1 M, and mixtures thereof. For example, electrolyte solutions can be, but are not limited to, about 0.1 N HCl or less, about 0.01 N HCl or less, about 0.001 N HCl or less, about 0.1 M NaCl or less, about 0.01 M NaCl or less, about 0.001 M NaCl or less, and mixtures thereof. Of these electrolyte solutions, 0.01 N HCl and/or 0.1 M NaCl, are most representative of fasted human physiological conditions, owing to the pH and ionic strength conditions of the proximal gastrointestinal tract.

Electrolyte concentrations of 0.001 N HCl, 0.01 N HCl, and 0.1 N HCl correspond to pH 3, pH 2, and pH 1, respectively. Thus, a 0.01 N HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed bisphosphonate particles of the invention (redispersed in an aqueous, biorelevant, or any other suitable media) have an effective average particle size of less than about 2000 nm, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. Such methods suitable for measuring effective average particle size are known to a person of ordinary skill in the art.

Redispersibility can be tested using any suitable means known in the art. See e.g., the example sections of U.S. Patent No. 6,375,986 for "Solid Dose Nanoparticulate Compositions Comprising a Synergistic Combination of a Polymeric Surface Stabilizer and Dioctyl Sodium Sulfosuccinate."

6. Nanoparticulate Bisphosphonate Compositions Used in Conjunction with Other Active Agents The compositions of the invention comprising at least one nanoparticulate bisphosphonate, such as alendronate, pamidronate, risedronate, etidronate, ibandronate, and zolendronic acid, can additionally comprise one or more compounds useful in treating bone resorption or related conditions. The compositions of the invention can be co-formulated with such other active agents, or the compositions of the invention can be co-administered or sequentially administered in conjunction with such active agents.

Exemplary additional active agents include, but are not limited to, calcium supplements, selective estrogen receptor modulators (e.g., raloxifene (EVISTA®)), hormones such as calcitonin (CALCIMAR® or MIACALCIN®), and or parathyroid hormone (including PTH (1-84) and PTH (1-34) (e.g., teriparatide (FORTEO®)).

C. Compositions

The invention provides compositions comprising at least one nanoparticulate bisphosphonate and at least one surface stabilizer. The surface stabilizers are preferably adsorbed to or associated with the surface of the bisphosphonate particles. If the bisphosphonate particles are present in a complex with a cation, then the surface stabilizer is adsorbed to or associated with the surface of the bisphosphonate complex. Surface stabilizers useful herein do not chemically react with the bisphosphonate particles or itself. Preferably, individual molecules of the surface stabilizer are essentially free of intermolecular cross-linkages. In another embodiment, the nanoparticulate bisphosphonate compositions of the invention can comprise two or more surface stabilizers.

The invention also includes nanoparticulate bisphosphonates complexed with a multivalent cation, such as $Ca^{++}$ or other salt that is poorly water soluble, or esters or prodrugs that are poorly water soluble. Such complexing enables particle size reduction of the bisphosphonate in an aqueous media.

The nanoparticulate bisphosphonate compositions can comprise one or more non-toxic physiologically acceptable carriers, adjuvants, or vehicles, collectively referred to as carriers. The compositions can be formulated into any pharmaceutically acceptable dosage form, including but not limited to oral and injectable dosage forms.

1. Bisphosphonates

The methods and compositions of the invention comprise a bisphosphonate, including but not limited to alendronate, pamidronate, risedronate, etidronate, ibandronate, and zolendronic acid. The bisphosphonate when applicable, may be present either in the form of one substantially optically pure enantiomer or as a mixture, racemic or otherwise, of enantiomers. The bisphosphonates of the invention are also referred to interchangeably as the "compounds of bisphosphonate." The bisphosphonates of the invention correspond to the chemical formula:

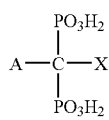

wherein:

A and X are independently selected from the group consisting of H, OH, halogen, $NH_2$, SH, phenyl, C1-C30 alkyl, C1-C30 substituted alkyl, C1-C10 alkyl or dialkyl substituted $NH_2$, C1-$C_{10}$ alkoxy, C1-C10 alkyl or phenyl substituted thio, C1-C10 alkyl substituted phenyl, pyridyl, furanyl, pyrrolidinyl, imidazonyl, and benzyl.

In the foregoing chemical formula, the alkyl groups can be straight, branched, or cyclic, provided sufficient atoms are selected for the chemical formula. The C1-C30 substituted alkyl can include a wide variety of substituents, non-limiting examples which include those selected from the group consisting of phenyl, pyridyl, furanyl, pyrrolidinyl, imidazonyl, NH2, C1-C10 alkyl or dialkyl substituted $NH_2$, OH, SH, and C1-C10 alkoxy.

The foregoing chemical formula is also intended to encompass complex carbocyclic, aromatic and hetero atom structures for the A and/or X substituents, non-limiting examples of which include naphthyl, quinolyl, isoquinolyl, adamantyl, and chlorophenylthio.

Preferred structures are those in which A is selected from the group consisting of H, OH, and halogen, and X is selected from the group consisting of C1-C30 alkyl, C1-C30 substituted alkyl, halogen, and C1-CIO alkyl or phenyl substituted thio. More preferred structures are those in which A is selected from the group consisting of H, OH, and Cl, and X is selected from the group consisting of C1-C30 alkyl, C1-C30 substituted alkyl, Cl, and chlorophenylthio. Most preferred is when A is OH and X is a 3-aminopropyl moiety, so that the resulting compound is a 4-amino-1,-hydroxybutylidene- 1,1-bisphosphonate, i.e., alendronate.

Pharmaceutically acceptable salts and derivatives of the bisphosphonates are also useful herein. Non-limiting examples of salts include those selected from the group consisting alkali metal, alkaline metal, ammonium, and mono-, di, tri-, or tetra-C1-C30-alkyl-substituted ammonium. Preferred salts are those selected from the group consisting of sodium, potassium, calcium, magnesium, and ammonium salts. Non-limiting examples of derivatives include those selected from the group consisting of esters, hydrates, and amides.

"Pharmaceutically acceptable" as used herein means that the salts and derivatives of the bisphosphonates have the same general pharmacological properties as the free acid from which they are derived and are acceptable from a toxicity viewpoint.

The terms "bisphosphonate" and "bisphosphonates," as used herein in referring to the therapeutic agents of the invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 70 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 70 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990, and U.S. Pat. No. 5,019,651, to Kieczykowski, used May 28, 1991, both of which are incorporated by reference herein in their entirety.

Cycloheptylaminomethylene-1,1-bisphosphonic acid, YM 175, Yamanouchi (cimadronate), as described in U.S. Pat. No. 4,970,335.

1,1-dichloromethylene-1,1-diphosphonic acid (clodronic acid), and the disodium salt (clodronate, Procter and Gamble), described in Belgium Patent 672,205 (1966) and *J Org. Chem* 32, 4111 (1967).

1-hydroxy-3-(1-pyrrolidinyl)-propylidene-1,1-bisphosphonic acid (EB-1053).

11-hydroxyethane-1,1-diphosphonic acid (etidronic acid).

1-hydroxy-3-(N-methyl-N-pentylamino)propylidene-1,1-bisphosphonic acid, also known as BM-2-210955, Boehringer-Mannheim (ibandronate), described in U.S. Pat. No. 4,927,814.

[(cycloheptyl-amino) methylene] bisphosphonic acid (incadronic acid).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate), described in U.S. Pat. No. 4,761,406.

1-hydroxy-2-(3-pyridinyl)-ethylidene-1,1-bisphosphonic acid (risedronate).

(4-chlorophenyl)thiomethane-1,1-disphosphonic acid (tiludronate), described in U.S. Pat. No. 4,876,248.

1-hydroxy-2-(1H-imidazol-1-yl)ethylidene-1,1-bisphosphonic acid (zolendronate).

Exemplary bisphosphonates include but are not limited to alendronate, incadronate, olpadronate, cimadronate, clodronate, tiludronate, etidronate, neridronate, ibandronate, risedronate, piridronate, pamidronate, zolendronate, pharmaceutically acceptable salts thereof, such as alendronate sodium and alendronate monosodium trihydrate, and mixtures thereof.

2. Surface Stabilizers

Combinations of more than one surface stabilizer can be used in the nanoparticulate bisphosphonate compositions of the invention. Suitable surface stabilizers include, but are not limited to, known organic and inorganic pharmaceutical excipients. Such excipients include various polymers, low molecular weight oligomers, natural products, and surfactants. Surface stabilizers include nonionic, ionic, anionic, cationic, and zwitterionic surfactants.

Representative examples of surface stabilizers include but are not limited to hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is C18H37CH2(CON(CH3)-CH2(CHOH)4(CH20H)2 (Eastman Kodak Co.); decanoyl-N-methylglucamide; n-decyl (-D-glucopyranoside; n-decyl (-D-maltopyranoside; n-dodecyl (-D-glucopyranoside; n-dodecyl (-D-maltoside; heptanoyl-N-methylglucamide; n-heptyl-(-D-glucopyranoside; n-heptyl (-D-thioglucoside; n-hexyl (-D-glucopyranoside; nonanoyl-N-methylglucamide; n-noyl (-D-glucopyranoside; octanoyl-N-methylglucamide; n-octyl-(-D-glucopyranoside; octyl (-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate. Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15dimethyl hydroxyethyl ammonium chloride or bromide, coconut dimethyl hydroxyethyl ammonium chloride or bromide, myristyl trimethyl ammonium methyl sulfate, lauryl dimethyl benzyl ammonium chloride or bromide, lauryl dimethyl (ethenoxy)4 ammonium chloride or bromide, N-alkyl (C12-18)dimethyl-benzyl ammonium chloride, N-alkyl (C14-18)dimethyl-benzyl ammonium chloride, N-tetradecyldimethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl (C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336), POLYQUAT, tetrabutylammonium bromide, benzyl trimethylammonium bromide, choline esters (such as choline esters of fatty acids), benzalkonium chloride, stearalkonium chloride compounds (such as stearyltrimonium chloride and distearyldimonium chloride), cetyl pyridinium bromide or chloride, halide salts of quaternized polyoxyethylalkylamines, MIRAPOL and ALKAQUAT (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula NR1R2R3R4(+). For compounds of the formula NR1R2R3R4(+):

(i) none of R1-R4 are CH3;
(ii) one of R1-R4 is CH3;
(iii) three of R1-R4 are CH3;
(iv) all of R1-R4 are CH3;
(v) two of R1-R4 are CH3, one of R1-R4 is C6H5CH2, and one of R1-R4 is an alkyl chain of seven carbon atoms or less;
(vi) two of R1-R4 are CH3, one of R1-R4 is C6H5CH2, and one of R1-R4 is an alkyl chain of nineteen carbon atoms or more;
(vii) two of R1-R4 are CH3 and one of R1-R4 is the group C6H5(CH2)n, where n>1;
(viii) two of R1-R4 are CH3, one of R1-R4 is C6H5CH2, and one of R1-R4 comprises at least one heteroatom;
(ix) two of R1-R4 are CH3, one of R1-R4 is C6H5CH2, and one of R1-R4 comprises at least one halogen;
(x) two of R1-R4 are CH3, one of R1-R4 is C6H5CH2, and one of R1-R4 comprises at least one cyclic fragment;
(xi) two of R1-R4 are CH3 and one of R1-R4 is a phenyl ring; or
(xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated herein by reference.

Povidone Polymers

Povidone polymers are exemplary surface stabilizers for use in formulating an injectable nanoparticulate bisphosphonate composition. Povidone polymers, also known as polyvidon(e), povidonum, PVP, and polyvinylpyrrolidone, are sold under the trade names Kollidon® (BASF Corp.) and Plasdone® (ISP Technologies, Inc.). They are polydisperse macromolecular molecules, with a chemical name of 1-ethenyl-2-pyrrolidinone polymers and 1-vinyl-2-pyrrolidinone polymers. Povidone polymers are produced commercially as a series of products having mean molecular weights ranging from about 10,000 to about 700,000 daltons. To be useful as a surface modifier for a drug compound to be administered to a mammal, the povidone polymer must have a molecular weight of less than about 40,000 daltons, as a molecular weight of greater than 40,000 daltons would have difficulty clearing the body.

Povidone polymers are prepared by, for example, Reppe's process, comprising: (1) obtaining 1,4-butanediol from acetylene and formaldehyde by the Reppe butadiene synthesis; (2) dehydrogenating the 1,4-butanediol over copper at 200° to form γ-butyrolactone; and (3) reacting γ-butyrolactone with ammonia to yield pyrrolidone. Subsequent treatment with acetylene gives the vinyl pyrrolidone monomer. Polymerization is carried out by heating in the presence of $H_2O$ and $NH_3$. See *The Merck Index*, $10^{th}$ Edition, pp. 7581 (Merck & Co., Rahway, N.J., 1983).

The manufacturing process for povidone polymers produces polymers containing molecules of unequal chain length, and thus different molecular weights. The molecular weights of the molecules vary about a mean or average for each particular commercially available grade. Because it is difficult to determine the polymer's molecular weight directly, the most widely used method of classifying various molecular weight grades is by K-values, based on viscosity measurements. The K-values of various grades of povidone polymers represent a function of the average molecular weight, and are derived from viscosity measurements and calculated according to Fikentscher's formula.

The weight-average of the molecular weight, Mw, is determined by methods that measure the weights of the individual molecules, such as by light scattering. Table 1 provides molecular weight data for several commercially available povidone polymers, all of which are soluble.

TABLE 1

| Povidone | K-Value | Mv (Daltons)** | Mw (Daltons)** | Mn (Daltons)** |
|---|---|---|---|---|
| Plasdone C-15 ® | 17 ± 1 | 7,000 | 10,500 | 3,000 |
| Plasdone C-30 ® | 30.5 ± 1.5 | 38,000 | 62,500* | 16,500 |
| Kollidon 12 PF ® | 11-14 | 3,900 | 2,000-3,000 | 1,300 |
| Kollidon 17 PF ® | 16-18 | 9,300 | 7,000-11,000 | 2,500 |
| Kollidon 25 ® | 24-32 | 25,700 | 28,000-34,000 | 6,000 |

*Because the molecular weight is greater than 40,000 daltons, this povidone polymer is not useful as a surface stabilizer for a drug compound to be administered parenterally (i.e., injected).
**Mv is the viscosity-average molecular weight, Mn is the number-average molecular weight, and Mw is the weight average molecular weight. Mw and Mn were determined by light scattering and ultra-centrifugation, and Mv was determined by viscosity measurements.

Based on the data provided in Table 1, exemplary useful commercially available povidone polymers include, but are not limited to, Plasdone C-15®, Kollidon 12 ®, Kollidon 17 PF®, and Kollidon 25®.

3. Other Pharmaceutical Excipients

The nanoparticulate bisphosphonate compositions of the invention may also comprise one or more binding agents, filling agents, penetration enhancers, lubricating agents, suspending agents, sweeteners, flavoring agents, preservatives, buffers, wetting agents, disintegrants, effervescent agents, and other excipients. Such excipients are known in the art.

Typical bonding agents or binders are starch paste or methyl cellulose.

Examples of filling agents are lactose monohydrate, lactose anhydrous, and various starches. Examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC®).

Suitable lubricants, including agents that act on the flowability of the powder to be compressed, are colloidal silicon dioxide, such as Aerosil® 200, talc, stearic acid, magnesium stearate, calcium stearate, and silica gel.

Aqueous suspensions comprising the nanoparticulate bisphosphonate can be in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acadia.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Examples of buffers are phosphate buffers, citrate buffers and buffers made from other organic acids.

Examples of wetting or dispersing agents are a naturally-occurring phosphatide, for example, lecithin or condensation products of n-alkylene oxide with fatty acids, for example, polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyethylene sorbitan monooleate.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Complexing Agents

The nanoparticulate bisphosphonate can be complexed with a multivalent or divalent cation, such as $Ca^{++}$, $Zn^{2+}$, $Mn^{2+}$, or other salt that is poorly water soluble, or esters or prodrugs that are poorly water soluble. Such complexing enables particle size reduction of the bisphosphonate in an aqueous media.

5. Enhancers

The bisphosphonate component of the composition may be accompanied, for example, by an enhancer compound to modify the bioavailability or therapeutic effect of the active ingredient. As used herein, the term "enhancer" refers to a compound which is capable of enhancing the absorption and/or bioavailability of an active ingredient by promoting net transport across the gastro-intestinal tract in an animal, such as a human. Enhancers include but are not limited to medium chain fatty acids; salts, esters, ethers and derivatives thereof, including glycerides and triglycerides; non-ionic surfactants such as those that can be prepared by reacting ethylene oxide with a fatty acid, a fatty alcohol, an alkylphenol or a sorbitan or glycerol fatty acid ester; cytochrome P450 inhibitors, P-glycoprotein inhibitors and the like; and mixtures of two or more of these agents.

6. Solid Dosage Forms of Nanoparticulate Bisphosphonates

The multi-particulate or monolithic oral nanoparticulate bisphosphonate compositions of the invention preferably include at least one chelating agent, sodium caprylate, and a pH-sensitive coating.

Conventional tablets of bisphosphonates, such as FOSAMAX®, ACTONEL®, DIDRONEL®, and BONIVA®, have limited bioavailability. While bisphosphonates are water soluble, which is generally associated with high bioavailability, upon administration conventional bisphosphonates often complex with cations in the surrounding environment and precipitate, thereby inhibiting cellular diffusion. The presence of a chelating agent in the oral dosage forms of the invention is proposed to enhance the bioavailability of the active ingredient by bonding to the cations in the gastrointestinal tract instead of bisphosphonate.

Typical chelating agents are α-hydroxy fatty acids, palmitic acid, phytic acid, (lactoferrin), α-hydroxy acids (for example citric acid, lactic acid, malic acid), humic acid, bile acid, bile extracts, bilirubin, biliverdin, ethylene diamine tetracetic acid ("EDTA") and ethyleneglycol-b-s-(beta-aminoethyl ether) -N,N,N,$N^1$-tetracetic acid ("EGTA") and their derivatives, unsaturated fatty acids and their derivatives (for example γ-linolenic acid, linolic acid, oleic acid), folic acid and its derivatives, and alaninediacetic acid. The preferred chelating agents are EDTA and EGTA. The most preferred chelating agent is EDTA.

The pH-sensitive coatings useful in the practice of the present invention are preferably anionic polymers of methacrylic acid, methacrylates and their phthalate esters commercially available as the Eudragit® series of polymers and mixtures thereof.

Bisphosphonate bioavailability is further improved by mixing particles of the bisphosphonate with sodium caprylate particles thereby allowing a smaller dose to give the same in vivo blood levels as larger dosage amounts required in the past.

Moreover, the bisphosphonate particles can be coated with a pH-sensitive coating, which delays diffusion of bisphosphonate particles until the composition reaches the intestine. Accordingly, the coated particles lessen possible unwanted side effects resulting from the release of currently used bisphosphonates in the gastrointestinal tract.

A multi-particulate or monolithic oral modified release composition according to the invention may be incorporated into any suitable dosage form. Typically, the dosage form will be a blend of the different populations of particles of bisphosphonate for the treatment of disorders relating to abnormal bone resorption, particles of sodium caprylate and of a chelating agent. The particles are preferably coated with a pH-sensitive coating. The particles may be blended and the blend filled into suitable capsules, such as hard or soft gelatin capsules. The ingredient-containing particles may be compressed (optionally with additional excipients) into mini-tablets.

The composition according to the invention may comprise at least two populations of bisphosphonate-comprising particles which have different in vitro dissolution profiles. Such dissolution profiles can be altered, for example, by varying the components present in the two or more populations or by varying the particle size of the bisphosphonate particles present in each population.

Preferably, in operation the composition of the invention and the solid oral dosage forms comprising the composition do not release the bisphosphonate until the active ingredient reaches the intestine. Release of the bisphosphonate is delayed, as described above, by the use of a pH sensitive coating on the active ingredient, sodium caprylate and preferably, a chelating agent.

7. Injectable Nanoparticulate Bisphosphonate Formulations of the Invention

The injectable dosage forms of the nanoparticulate bisphosphonate compositions of the invention preferably comprise at least one nanoparticulate bisphosphonate and at least one surface stabilizer, wherein the nanoparticulate bisphosphonate is complexed with a salt or a poorly water soluble prodrug. The complex can also comprise a multivalent cation, preferably a divalent cation, such as $Ca^{++}$, $Zn^{2+}$, or $Mn^{2+}$. The presence of such a multivalent or divalent cation results in dramatically reduced side effects and irritancy of the administered composition.

In one embodiment, the composition is formulated into an injectable dosage form for intramuscular or subcutaneous injection, wherein the bisphosphonate concentration in composition ranges from about 0.1% up to about 60% (w/v).

In an exemplary embodiment, the invention provides nanoparticulate bisphosphonate that can comprise high drug concentrations in low injection volumes. Exemplary compositions comprise, based on % w/w:

| | |
|---|---|
| bisphosphonate | 5-50% |
| surface stabilizer | 0.1-50% |
| preservatives | 0.05-0.25% |
| pH adjusting agent | pH about 6 to about 7 |
| water for injection | q.s. |

Exemplary preservatives include methylparaben (about 0.18% based on % w/w), propylparaben (about 0.02% based on % w/w), phenol (about 0.5% based on % w/w), and benzyl alcohol (up to 2% v/v). An exemplary pH adjusting agent is sodium hydroxide, and an exemplary liquid carrier is sterile water for injection. Other useful preservatives, pH adjusting agents, and liquid carriers are well-known in the art.

In one embodiment of the invention, provided are injectable nanoparticulate bisphosphonate compositions that form a subcutaneous or intramuscular depot to provide continuous delivery of the drug to the mammal over a period of time. The period of time can be up to about 1 week, up to about 2 weeks, up to about 3 weeks, up to about 4 weeks, up to about 1 month, up to about 2 months, up to about 3 months, up to about 4 months, up to about 5 months, up to about 6 months, up to about 7 months, up to about 8 months, up to about 9 months, up to about 10 months, up to about 11 months, up to about 12 months, up to about 18 months, up to about 2 years, up to about 30 months, up to about 3 years, up to about 3½ years, up to about 4½ years, up to about 4½ years, or up to about 5 years or once a lifetime.

8. Nanoparticulate Bisphosphonate Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise at least one bisphosphonate having an effective average particle size of less than about 2000 nm (i.e., 2 microns). In other embodiments of the invention, the bisphosphonate nanoparticles have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

An "effective average particle size of less than about 2000 nm" means that at least 50% of the bisphosphonate particles have a particle size less than the effective average, by weight, i.e., less than about 2000 nm. If the "effective average particle size" is less than about 1900 nm, then at least about 50% of the bisphosphonate particles have a size of less than about 1900 nm, when measured by the above-noted techniques. The same is true for the other particle sizes referenced above. In other embodiments, at least about 60%, at least about 70%, at least about 80%, at least about 90%, at least about 95%, or at least about 99% of the bisphosphonate particles have a particle size less than the effective average, i.e., less than about 2000 nm, less than about 1900 nm, less than about 1800 nm, etc.

In the invention, the value for D50 of a nanoparticulate bisphosphonate composition is the particle size below which 50% of the bisphosphonate particles fall, by weight. Similarly, D90 is the particle size below which 90% of the bisphosphonate particles fall, by weight.

9. Concentration of Nanoparticulate Bisphosphonate Compound and Surface Stabilizers The relative amounts of bisphosphonate and one or more surface stabilizers can vary widely. The optimal amount of the individual components depends, for example, upon the particular bisphosphonate, and the physical and chemical attributes of the surface stabilizer(s) selected, such as the hydrophilic lipophilic balance (HLB), melting point, and the surface tension of water solutions of the stabilizer, etc.

Preferably, the concentration of bisphosphonate can vary from about 99.5% to about 0.001%, from about 95% to about 0.1%, or from about 90% to about 0.5%, by weight, based on the total combined weight of the bisphosphonate and at least one surface stabilizer, not including other excipients. Higher concentrations of bisphosphonate are generally preferred from a dose and cost efficiency standpoint.

Preferably, the concentration of surface stabilizer can vary from about 0.5% to about 99.999%, from about 5.0% to about 99.9%, or from about 10% to about 99.5%, by weight, based on the total combined dry weight of bisphosphonate and at least one surface stabilizer, not including other excipients.

D. Method of Making Nanoparticulate Bisphosphonate Compositions

Nanoparticulate bisphosphonate compositions can be made using any suitable method known in the art such as, for example, milling, homogenization, precipitation, or supercritical fluid particle generation techniques. When the bisphosphonate particle is to be reduced in size in an aqueous media, then the bisphosphonate is first complexed with a multivalent or divalent cation, such as $Ca^{++}$, $Zn^{2+}$, or $Mn^{2+}$, or other salt that is poorly water soluble, or esters or prodrugs that are poorly water soluble, to reduce the water solubility of the drug.

Exemplary methods of making nanoparticulate active agent compositions are described in U.S. Pat. No. 5,145,684. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated herein by reference.

For particle size reducing in an aqueous media, the bisphosphonate is complexed with a multivalent or divalent cation, such as $Ca^{++}$, $Zn^{2+}$, or $Mn^{2+}$, to reduce the water solubility of the drug. The resultant nanoparticulate bisphosphonate compositions or dispersions can be utilized in solid, semi-solid, or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

An exemplary method of preparing the nanoparticulate bisphosphonate formulations of the invention comprises the steps of: (1) dispersing the desired dosage amount of a bisphosphonate complex in a liquid dispersion media in which the drug is poorly soluble; and (2) mechanically reducing the particle size of the bisphosphonate complex to an effective average particle size of less than about 2000 nm. A surface stabilizer can be added to the dispersion media either before, during, or after particle size reduction of the bisphosphonate complex. The liquid dispersion medium can be maintained at a physiologic pH, for example, within the range of from about 3.0 to about 8.0 during the size reduction process; more preferably within the range of from about 5.0 to about 7.5 during the size reduction process. Preferably, the dispersion media used for the size reduction process is aqueous, although any dispersion media in which the bisphosphonate is poorly soluble can be used, such as safflower oil, ethanol, t-butanol, glycerin, polyethylene glycol (PEG), hexane, or glycol.

Using a particle size reduction method, the particle size of the bisphosphonate is reduced to an effective average particle size of less than about 2000 nm. Effective methods of providing mechanical force for particle size reduction of the bisphosphonate include ball milling, media milling, and homogenization, for example, with a Microfluidizer® (Microfluidics Corp.). Ball milling is a low energy milling process that uses milling media, drug, stabilizer, and liquid. The materials are placed in a milling vessel that is rotated at optimal speed such that the media cascades and reduces the drug particle size by impaction. The media used must have a high density as the energy for the particle reduction is provided by gravity and the mass of the attrition media.

1. Bisphosphonate Particle Size Reduction Using Milling

Media milling is a high energy milling process. Bisphosphonate complex, surface stabilizer, and liquid are placed in a reservoir and re-circulated in a chamber comprising grinding media and a rotating shaft/impeller. The rotating shaft agitates the grinding media which subjects the bisphosphonate complex to impaction and sheer forces, thereby reducing the bisphosphonate complex particle size.

The bisphosphonate complex can be added to a liquid media in which it is essentially insoluble to form a premix. The surface stabilizer can be present in the premix or it can be added to the bisphosphonate complex dispersion following particle size reduction. The premix can be used directly by subjecting it to mechanical means to reduce the average bisphosphonate complex particle size in the dispersion to less than about 2000 nm. It is preferred that the premix be used directly when a ball mill is used for attrition. Alternatively, the bisphosphonate complex and at least one surface stabilizer can be dispersed in the liquid media using suitable agitation, e.g., a Cowles type mixer, until a homogeneous dispersion is observed in which there are no large agglomerates visible to the naked eye. It is preferred that the premix be subjected to such a pre-milling dispersion step when a re-circulating media mill is used for attrition.

The mechanical means applied to reduce the bisphosphonate complex particle size can take the form of a dispersion mill. Suitable dispersion mills include a ball mill, an attritor mill, a vibratory mill, and media mills such as a sand mill and a bead mill. A media mill is preferred due to the relatively shorter milling time required to provide the desired reduction in particle size. For media milling, the apparent viscosity of the premix is preferably from about 100 to about 1000 centipoise, and for ball milling the apparent viscosity of the premix is preferably from about 1 up to about 100 centipoise. Such ranges tend to afford an optimal balance between efficient particle size reduction and media erosion.

The attrition time can vary widely and depends primarily upon the particular mechanical means and processing conditions selected. For ball mills, processing times of up to five days or longer may be required. Alternatively, processing times of less than 1 day (residence times of one minute up to several hours) are possible with the use of a high shear media mill.

The bisphosphonate complex particles can be reduced in size at a temperature which does not significantly degrade the bisphosphonate complex molecule. Processing temperatures of less than about 30 to less than about 40° C. are ordinarily preferred. If desired, the processing equipment can be cooled with conventional cooling equipment. Control of the temperature, e.g., by jacketing or immersion of the milling chamber in ice water, is contemplated. Generally, the method of the invention is conveniently carried out under conditions of ambient temperature and at processing pressures which are safe and effective for the milling process. Ambient processing pressures are typical of ball mills, attritor mills, and vibratory mills.

Grinding Media

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. Zirconium oxide, such as 95% ZrO stabilized with magnesia, zirconium silicate, ceramic, stainless steel, titania, alumina, 95% ZrO stabilized with yttrium, glass grinding media, and polymeric grinding media are exemplary grinding materials.

The grinding media can comprise particles that are preferably substantially spherical in shape, e.g., beads, consisting essentially of polymeric resin or other suitable material. Alternatively, the grinding media can comprise a core having a coating of a polymeric resin adhered thereon. The polymeric resin can have a density from about 0.8 to about 3.0 g/cm$^3$.

In general, suitable polymeric resins are chemically and physically inert, substantially free of metals, solvent, and monomers, and of sufficient hardness and friability to enable them to avoid being chipped or crushed during grinding. Suitable polymeric resins include crosslinked polystyrenes, such as polystyrene crosslinked with divinylbenzene; styrene copolymers; polycarbonates; polyacetals, such as Delrin® (E.I. du Pont de Nemours and Co.); vinyl chloride polymers and copolymers; polyurethanes; polyamides; poly(tetrafluoroethylenes), e.g., Teflone® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

In a preferred grinding process the bisphosphonate complex particles are made continuously. Such a method comprises continuously introducing the bisphosphonate complex into a milling chamber, contacting the compounds with grinding media while in the chamber to reduce the particle size, and continuously removing the nanoparticulate bisphosphonate complex from the milling chamber.

The grinding media is separated from the milled nanoparticulate bisphosphonate complex using conventional separation techniques, in a secondary process such as by simple filtration, sieving through a mesh filter or screen, and the like. Other separation techniques such as centrifugation may also be employed.

Sterile Product Manufacturing

Development of injectable compositions requires the production of a sterile product.

The manufacturing process of the present invention is similar to typical known manufacturing processes for sterile suspensions. A typical sterile suspension manufacturing process flowchart is as follows:

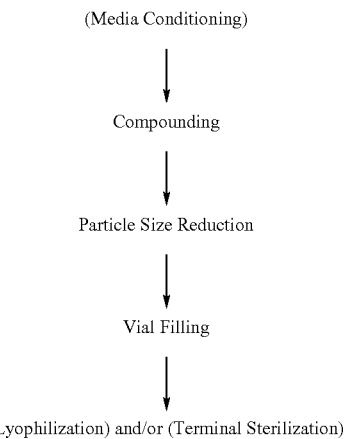

As indicated by the optional steps in parentheses, some of the processing is dependent upon the method of particle size reduction and/or method of sterilization. For example, media conditioning is not required for a milling method that does not use media. If terminal sterilization is not feasible due to chemical and/or physical instability, aseptic processing can be used.

2. Bisphosphonate Particle Size Reduction Using Homogenization

Homogenization is a technique that does not use milling media. Bisphosphonate complex, surface stabilizer, and liquid (or drug and liquid with the surface stabilizer added after particle size reduction) constitute a process stream propelled into a process zone, which in the Microfluidizer® is called the Interaction Chamber. The product to be treated is inducted into the pump, and then forced out. The priming valve of the Microfluidizer® purges air out of the pump. Once the pump is filled with product, the priming valve is closed and the product is forced through the interaction chamber. The geometry of the interaction chamber produces powerful forces of sheer, impact, and cavitation which are responsible for particle size reduction. Specifically, inside the interaction chamber, the pressurized product is split into two streams and accelerated to extremely high velocities. The formed jets are then directed toward each other and collide in the interaction zone. The resulting product has very fine and uniform particle or droplet size. The Microfluidizer® also provides a heat exchanger to allow cooling of the product. U.S. Pat. No. 5,510,118, which is specifically incorporated by reference, refers to a process using a Microfluidizer.®

3. Bisphosphonate Particle Size Reduction Using Precipitation

Another method of forming the desired nanoparticle bisphosphonate dispersion is by microprecipitation. This is a method of preparing stable dispersions of nanoparticulate particles of the composition according to the invention in the presence of one or more surface stabilizers and one or more colloid stability enhancing surface active agents free of any trace toxic solvents or solubilized heavy metal impurities. Such a method comprises, for example, (1) dissolving the bisphosphonate composition according to the invention, in a suitable solvent with mixing; (2) adding the formulation from step (1) with mixing to a solution comprising at least one surface stabilizer to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate bisphosphonate composition according to the invention can be utilized in a pharmaceutically acceptable dosage form.

E. Methods of Using the Formulations and Compositions of the Invention

The nanoparticulate bisphosphonate compositions of the invention are useful in treatments including but not limited to the treatment of disorders relating to abnormal bone resorption.

The methods and compositions of the invention are useful for inhibiting bone resorption and for treating and preventing abnormal bone resorption and conditions associated therewith. Such conditions include both generalized and localized bone loss.

Generalized bone loss is often associated with osteoporosis. Osteoporosis is most common in post-menopausal women, whose estrogen production has been greatly diminished. However, osteoporosis can also be steroid-induced and has been observed in males due to age. Osteoporosis can be induced by disease, e.g., rheumatoid arthritis, it can be induced by secondary causes, e.g., glucocorticoid therapy, or it can about with no identifiable cause, i.e., osteoporosis. In the present invention, preferred methods include the treatment or prevention of abnormal bone resorption in osteoporotic humans.

Localized bone loss has been associated with periodontal disease, bone fractures, and with periprosthetic osteolysis (in other words where bone resorption has occurred in proximity to a prosthetic implant).

Generalized or localized bone loss can occur from disuse, which is often a problem for those confined to a bed or a wheelchair, or for those who have an immobilized limb set in a cast or in traction.

The methods and compositions of the invention are useful for treating and/or preventing the following conditions or disease states: osteoporosis, which can include post-menopausal osteoporosis, steroid-induced osteoporosis, male osteoporosis, disease-induced osteoporosis, idiopathic osteoporosis; Paget's disease; abnormally increased bone turnover; periodontal disease; localized bone loss associated with periprosthetic osteolysis; and bone fractures.

Nanoparticulate bisphosphonate compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. The formulations may also include biodegradable polymers and lipid complexes.

The injectable formulations may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

The compositions and formulations of the invention can be administered to a subject by any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms "patient" and "subject" may be used interchangeably.

Solid dosage forms for oral administration include, but are not limited to, capsules, tablets, pills, powders, and granules. In such solid dosage forms, the multiparticles of the bisphosphonate, sodium caprylate and preferably, chelating agent, may be admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Besides such inert diluents, the composition can also include adjuvants, such as wetting agents, emulsifying and suspending agents, sweetening, flavoring, and perfuming agents.

"Therapeutically effective amount" as used herein with respect to the compounds of bisphosphonate, pharmaceutically acceptable salts thereof, esters thereof, and mixtures thereof, shall mean that dosage amount that provides the specific pharmacological response for which the bisphosphonate is administered in a significant number of subjects in need of treatment for disorders relating to abnormal bone resorption and related disorders. It is emphasized that "therapeutically effective amount," administered to a particular subject in a particular instance will not always be effective in treating the diseases described herein, even though such dosage is deemed a "therapeutically effective amount" by those skilled in the art.

One of ordinary skill will appreciate that effective amounts of the bisphosphonate can be determined empirically and can be employed in pure form or, where such forms exist, in pharmaceutically acceptable salt, ester, or prodrug form. Actual dosage levels of bisphosphonate in the nanoparticulate compositions of the invention may be varied to obtain an amount of the bisphosphonate that is effective to obtain a desired therapeutic response for a particular composition and method of administration. The selected dosage level therefore depends upon the desired therapeutic effect, the route of administration, the potency of the administered composition of the invention, the desired duration of treatment, and other factors.

Dosage unit compositions may contain such amounts of such sub-multiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e., a bone resorption inhibiting amount of the bisphosphonate is administered. For humans, an effective oral dose of bisphosphonate is typically from about 1.5 to about 6,000 µg/kg body weight and preferably about 10 to about 2,000 µg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis.

The present invention further provides a method of treating a patient suffering from disorders relating to abnormal bone resorption comprising administering a therapeutically effective amount of the formulation according to the invention to provide pulsed administration of the bisphosphonate. Advantages of this type of dosage form include reducing the dosing frequency required by conventional multiple IR dosage regimes while still maintaining the benefits derived from a pulsatile plasma profile. This reduced dosing frequency is advantageous in terms of patient compliance to have a formulation which may be administered at reduced frequency. The reduction in dosage frequency made possible by utilizing the compositions of the invention would contribute to reducing health care costs by reducing the amount of time spent by health care workers on the administration of bisphosphonates and, in particular, alendronate sodium in an IR dose for disorders relating to abnormal bone resorption.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An oral dosage form of a bisphosphonate composition comprising:
   particles consisting of at least one bisphosphonate complexed with a multivalent cation and having an effective average particle size of less than about 2000 nm, the bisphosphonate-cation complex particles having at least one surface stabilizer adsorbed on the surface of the particles;
   a permeation enhancer; and
   a chelating agent.

2. The composition of claim 1, wherein the chelating agent is selected from the group consisting of α-hydroxy fatty acids, palmitic acid, phytic acid, (lactolerrin),α-hydroxy acids, humic acid, bile acid, bile extracts, bilirubin, biliverdin, ethylene diamine tetracetic acid, ethyleneglycol-b-s-(beta-aminoethyl ether)-N,N,N,N$^1$-tetracetic acid ("EGTA"), EDTA derivatives, EGTA derivatives, unsaturated fatty acids, unsaturated fatty acid derivatives, folic acid, folic acid derivatives, and alaninediacetic acid.

3. The composition of claim 1, wherein the oral dosage form is coated with a pH-sensitive coating that delays dissolution of the bisphosphonate when administered orally.

4. The bisphosphonate composition of claim 3, wherein the composition reduces the occurrence of adverse gastrointestinal effects when compared to a similar composition having particles of the same at least one bisphosphonate, but which particles are greater than 2000 nm.

5. The composition of claim 1, wherein the permeation enhancer comprises sodium caprylate.

6. The bisphosphonate composition of claim 1, wherein the composition has substantially the same bioavailability when administered to a patient in a fed state than when administered to a patient in a fasted state.

7. The composition of claim 1, wherein the composition further comprises one or more pharmaceutically acceptable excipients, carriers, or a combination thereof.

8. The composition of claim 1, wherein the at least one surface stabilizer is present in an amount selected from the group consisting of from about 0.5% to about 99.999% by weight, from about 5.0% to about 99.9% by weight, and from about 10% to about 99.5% by weight, based on the total combined dry weight of the bisphosphonate-cation complex and at least one surface stabilizer, not including other excipients.

9. the composition of claim 1, wherein the bisphosphonate is present in an amount selected from the group consisting of from about 99.5% to about 0.001%, from about 95% to about 0.1%, and from about 90% to about 0.5%, by weight, based on the total combined weight of the bisphosphonate-cation complex and at least one surface stabilizer, not including other excipients.

10. The composition of claim 1, wherein the surface stabilizer is selected from the group consisting of an anionic surface stabilizer, a cationic surface stabilizer, a zwitterionic surface stabilizer, anon-ionic surface stabilizer, and an ionic surface stabilizer.

11. The composition of claim 1, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methyl-glucamide; n-decyl b-D-glucopyranoside; n-decyl b-D-maltopyranoside; n-dodecyl b-D-glucopyranoside; n-dodecyl b-D-maltoside; heptanoyl-N -methylglucamide; n-heptyl-b-

D-glucopyranoside; n-heptyl b-D-thioglucoside; n-hexyl b-D-glucopyranoside; nonanoyl-N-methylglucamide; n-noyl b-D-glucopyranoside; octanoyl-N-methylglucamide; n-octyl-b-D-glucopyranoside; octyl b-D-thioglucopyranoside; lysozyme, PEG-phospholipid, PEG-cholesterol, PEG-cholesterol derivative, PEG-vitamin A, PEG-vitamin E, random copolymers of vinyl acetate and vinyl pyrrolidone, a cationic polymer, a cationic biopolymer, a cationic polysaccharide, a cationic cellulosic, a cationic alginate, a cationic nonpolymeric compound, a cationic phospholipids, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, C12-15dimethyl hydroxyethyl ammonium chloride, C12-15dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)4 ammonium chloride, lauryl dimethyl (ethenoxy)4 ammonium bromide, N-alkyl (C12-18)dimethylbenzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C12-14) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12 trimethyl ammonium bromides, C15 trimethyl ammonium bromides, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, alkyl pyridinium salts; amines, amine salts, amine oxides, imide azolinium salts, protonated quaternary acrylamides, methylated quaternary polymers, and cationic guar.

12. The composition of claim 1, wherein the surface stabilizer is a povidone polymer having a molecular weight of about 40,000 daltons or less.

* * * * *